(12) United States Patent
Balaban et al.

(10) Patent No.: US 6,188,783 B1
(45) Date of Patent: Feb. 13, 2001

(54) METHOD AND SYSTEM FOR PROVIDING A PROBE ARRAY CHIP DESIGN DATABASE

(75) Inventors: David J. Balaban, San Rafael; Earl A. Hubbell, Los Angeles; Michael P. Mittmann, Palo Alto; Gloria Cheung, Cupertino; Josie Dai, San Jose, all of CA (US)

(73) Assignee: Affymetrix, Inc., Santa Clara, CA (US)

( * ) Notice: Under 35 U.S.C. 154(b), the term of this patent shall be extended for 0 days.

(21) Appl. No.: 09/122,304

(22) Filed: Jul. 24, 1998

Related U.S. Application Data

(60) Provisional application No. 60/053,842, filed on Jul. 25, 1997, provisional application No. 60/069,198, filed on Dec. 11, 1997, and provisional application No. 60/069,436, filed on Dec. 11, 1997.

(51) Int. Cl.[7] ................................................. G06K 9/00
(52) U.S. Cl. .................... 382/129; 382/129; 382/178; 422/68; 435/6; 435/287
(58) Field of Search .................... 382/129, 178; 422/68; 435/6, 287

(56) References Cited

U.S. PATENT DOCUMENTS

| | | | |
|---|---|---|---|
| 5,593,839 | * 1/1997 | Hubbell et al. | 435/6 |
| 5,800,992 | * 9/1998 | Fodor et al. | 435/6 |
| 5,856,101 | * 1/1999 | Hubbell et al. | 435/6 |
| 5,871,697 | 2/1999 | Rothberg et al. | 422/68.1 |
| 5,871,928 | * 2/1999 | Fodor et al. | 435/6 |
| 5,925,525 | * 7/1999 | Fodor et al. | 435/6 |
| 5,961,923 | * 10/1999 | Nova et al. | 422/68 |
| 5,974,164 | * 10/1999 | Chee | 382/129 |

OTHER PUBLICATIONS

PR Newswire, "Gene Logic to Use Affymetrix GeneChip Arrays to Build Gene Expression Datebase Products", Jan. 11, 1999.

Adams et al., "Complementary DNA Sequencing: Expressed Sequence Tags and Human Genome Project", *Science*, 252(5013): 1651–1656 (1991).

Frickett et al., "Development Of A Database for Nucleotide Sequences", *Mathematical Methods for DNA Sequences*, CRC Press, ED. Waterman, pp. 2–34 (1989).

Hara et al., "Subtractive cDNA Cloning Using Oligo(dT)$_{30}$–Latex And PCR: Isolation Of cDNA Clones Specific To Undifferentiated Human Embryonal Carcinoma Cells", *Nucleic Acids Res.*, 19(25):7097–7104 (1991).

Khan et al., "Single Pass Sequencing And Physical And Genetic Mapping Of Human Brain cDNAs", *Nat Genet.*, 2(3):180–185 (1992).

Matsubara et al., "Identification Of New Genes By Systematic Analysis Of cDNAs And Datebase Construction", *Curr. Opin. Biotechnol.*, 4(6):672–677 (1993).

\* cited by examiner

*Primary Examiner*—Matthew C. Bella
*Assistant Examiner*—M. Choobin
(74) *Attorney, Agent, or Firm*—Townsend and Townsend and Crew LLP

(57) ABSTRACT

Systems and method for organizing information relating to the design of polymer probe array chips including oligonucleotide array chips. A database model is provided which organizes information interrelating probes on a chip, genomic items investigated by the chip, and sequence information relating to the design of the chip. The model is readily translatable into database languages such as SQL. The database model scales to permit storage of information about large numbers of chips having complex designs.

9 Claims, 10 Drawing Sheets

METHOD AND SYSTEM FOR PROVIDING A PROBE ARRAY CHIP DESIGN DATABASE

CROSS-REFERENCE TO RELATED APPLICATIONS

The present application claims priority from U.S. Prov. App. No. 60/053,842 filed Jul. 25, 1997, entitled COMPREHENSIVE BIO-INFORMATICS DATABASE, from U.S. Prov. App. No. 60/069,198 filed on Dec. 11, 1997, entitled COMPREHENSIVE DATABASE FOR BIOINFORMATICS, and from U.S. Prov. App. No. 60/069,436, entitled GENE EXPRESSION AND EVALUATION SYSTEM, filed on Dec. 11, 1997. The contents of all three provisional applications are herein incorporated by reference.

The subject matter of the present application is related to the subject matter of the following three co-assigned applications filed on the same day as the present application: GENE EXPRESSION AND EVALUATION SYSTEM, METHOD AND APPARATUS FOR PROVIDING A BIOINFORMATICS DATABASE, METHOD AND SYSTEM FOR PROVIDING A POLYMORPHISM DATABASE. The contents of these three applications are herein incorporated by reference.

BACKGROUND OF THE INVENTION

The present invention relates to the collection and storage of information pertaining to chips for processing samples.

Devices and computer systems for forming and using arrays of materials on a substrate are known. For example, a PCT application WO92/10588, incorporated herein by reference for all purposes, describes techniques for sequencing or sequence checking nucleic acids and other materials. Arrays for performing these operations may be formed in arrays according to the methods of, for example, the pioneering techniques disclosed in U.S. Pat. No. 5,143,854 and U.S. Pat. No. 5,571,639, both incorporated herein by reference for all purposes.

According to one aspect of the techniques described therein, an array of nucleic acid probes is fabricated at known locations on a chip or substrate. A fluorescently labeled nucleic acid is then brought into contact with the chip and a scanner generates an image file indicating the locations where the labeled nucleic acids bound to the chip. Based upon the identities of the probes at these locations, it becomes possible to extract information such as the monomer sequence of DNA or RNA. Such systems have been used to form, for example, arrays of DNA that may be used to study and detect mutations relevant to cystic fibrosis, the P53 gene (relevant to certain cancers), HIV, and other genetic characteristics.

Computer-aided techniques for monitoring gene expression using such arrays of probes have also been developed as disclosed in U.S. patent application Ser. No. 08/828,952 and PCT publication No. WO 97/10365, the contents of which are herein incorporated by reference. Many disease states are characterized by differences in the expression levels of various genes either through changes in the copy number of the genetic DNA or through changes in levels of transcription (e.g., through control of initiation, provision of RNA precursors, RNA processing, etc.) of particular genes. For example, losses and gains of genetic material play an important role in malignant transformation and progression. Furthermore, changes in the expression (transcription) levels of particular genes (e.g., oncogenes or tumor suppressors), serve as signposts for the presence and progression of various cancers.

As can be seen, the probe array chips are designed to answer questions about genomic items, herein defined to include genes, expressed sequence tags (ESTs), gene clusters, and EST clusters. Associated with information about genomic items is genetic sequence information concerning the base sequences of genomic items. Probes are designed and selected for inclusion on a chip based on: 1) the identity of the genomic items to be investigated by the chip, 2) the sequence information associated with those genomic information, and 3) the type of information sought, e.g., expression analysis, polymorphism analysis, etc. The interrelationships, however, among probes, genomic items, and sequence information are, however, extremely complex, greatly complicating the tasks of designing chips, effectively exploiting chips that have already been designed, and efficiently interpreting the information generated by application of the chips.

Moreover, it is contemplated that the operations of chip design, construction, and application will occur on a very large scale. The quantity of information related to chip design to store and correlate is vast. What is needed is a system and method suitable for storing and organizing large quantities of information used in conjunction with the design of probe array chips.

SUMMARY OF THE INVENTION

The present invention provides systems and method for organizing information relating to the design of polymer probe array chips including oligonucleotide array chips. A database model is provided which organizes information interrelating probes on a chip, genomic items investigated by the chip, and sequence information relating to the design of the chip. The model is readily translatable into database languages such as SQL. The database model scales to permit storage of information about large numbers of chips having complex designs.

According to one aspect of the present invention, a computer-readable storage medium is provided. A relational database is stored on this medium. The relational database includes: a probe table including a plurality of probe records, each of the probe records specifying a polymer probe for use in one or more polymer probe arrays, a sequence item table including a plurality of sequence item records, each of the sequence item records specifying a nucleotide sequence to be investigated in the one or more polymer probe arrays, wherein there is a many-to-many relationship between the probe records and the sequence item records.

A further understanding of the nature and advantages of the inventions herein may be realized by reference to the remaining portions of the specification and the attached drawings.

DESCRIPTION OF SPECIFIC EMBODIMENTS

Biological Material Analysis System

One embodiment of the present invention operates in the context of a system for analyzing biological or other materials using arrays that themselves include probes that may be made of biological materials such as RNA or DNA. The VLSIPS™ and GeneChip™ technologies provide methods of making and using very large arrays of polymers, such as nucleic acids, on chips. See U.S. Pat. No. 5,143,854 and PCT Patent Publication Nos. WO 90/15070 and 92/10092, each of which is hereby incorporated by reference for all purposes. Nucleic acid probes on the chip are used to detect complementary nucleic acid sequences in a sample nucleic acid of interest (the "target" nucleic acid).

It should be understood that the probes need not be nucleic acid probes but may also be other polymers such as peptides. Peptide probes may be used to detect the concentration of peptides, polypeptides, or polymers in a sample. The probes must be carefully selected to have bonding affinity to the compound whose concentration they are to be used to measure.

Figure 1:
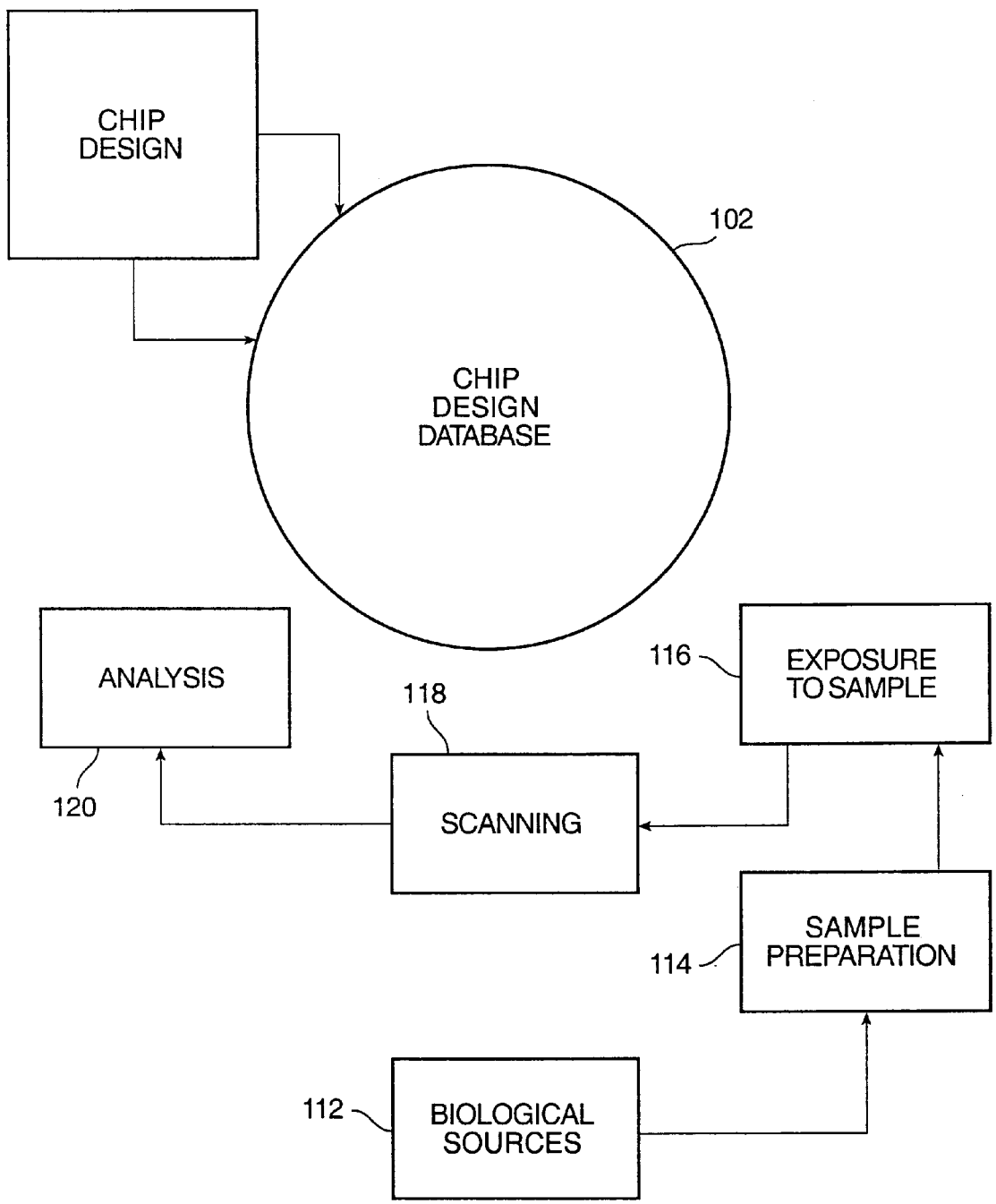
FIG. 1 illustrates an overall system and process for forming and analyzing arrays of biological materials such as DNA or RNA.

FIG. 1 illustrates an overall system 100 for forming and analyzing arrays of biological materials such as RNA or DNA. A part of system 100 is a chip design database 102. Chip design database 102 includes information about chip designs and the purposes of chips. Chip design database 102 facilitates large scale design, construction, and processing of chips.

A chip design system 104 is used to design arrays of polymers such as biological polymers such as RNA or DNA. Chip design system 104 may be, for example, an appropriately programmed Sun Workstation or personal computer or workstation, such as an IBM PC equivalent, including appropriate memory and a CPU. Chip design system 104 obtains inputs from a user regarding chip design objectives including characteristics of genes of interest, and other inputs regarding the desired features of the array. All of this information may be stored in chip design database 102. Optionally, chip design system 104 may obtain information regarding a specific genetic sequence of interest from chip design database 102 or from external databases such as GenBank. The output of chip design system 104 is a set of chip design computer files in the form of, for example, a switch matrix, as described in PCT application WO 92/10092, and other associated computer files. The chip design computer files form apart of chip design database 102. Systems for designing chips for sequence determination and expression analysis are disclosed in U.S. Pat. No. 5,571,639 and in PCT application WO 97/10365, the contents of which are herein incorporated by reference.

The chip design files are input to a mask design system (not shown) that designs the lithographic masks used in the fabrication of arrays of molecules such as DNA. The mask design system designs the lithographic masks used in the fabrication of probe arrays. The mask design system generates mask design files that are then used by a mask construction system (not shown) to construct masks or other synthesis patterns such as chrome-on-glass masks for use in the fabrication of polymer arrays.

The masks are used in a synthesis system (not shown). The synthesis system includes the necessary hardware and software used to fabricate arrays of polymers on a substrate or chip. The synthesis system includes a light source and a chemical flow cell on which the substrate or chip is placed. A mask is placed between the light source and the substrate/chip, and the two are translated relative to each other at appropriate times for deprotection of selected regions of the chip. Selected chemical reagents are directed through the flow cell for coupling to deprotected regions, as well as for washing and other operations. The substrates fabricated by the synthesis system are optionally diced into smaller chips. The output of the synthesis system is a chip ready for application of a target sample.

Information about the mask design, mask construction, probe array synthesis, and analysis systems is presented by way of background. A biological source 112 is, for example, tissue from a plant or animal. Various processing steps are applied to material from biological source 112 by a sample preparation system 114. These steps may include e.g., isolation of mRNA, precipitation of the MRNA to increase concentration, etc, synthesis of cDNA from MRNA, PCR amplification of fragments of interest. The result of the various processing steps is a target ready for application to the chips produced by the synthesis system 110.

The prepared samples include monomer nucleotide sequences such as RNA or DNA. When the sample is applied to the chip by a sample exposure system 116, the nucleotides may or may not bond to the probes. The nucleotides have been tagged with fluoroscein labels to determine which probes have bonded to nucleotide sequences from the sample. The prepared samples will be placed in a scanning system 118. Scanning system 118 includes a detection device such as a confocal microscope or CCD (charge-coupled device) that is used to detect the location where labeled receptors have bound to the substrate. The output of scanning system 118 is an image file(s) indicating, in the case of fluorescein labeled receptor, the fluorescence intensity (photon counts or other related measurements, such as voltage) as a function of position on the substrate. These image files also form a part of chip design database 102. Since higher photon counts will be observed where the labeled receptor has bound more strongly to the array of polymers, and since the monomer sequence of the polymers on the substrate is known as a function of position, it becomes possible to determine the sequence(s) of polymer (s) on the substrate that are complementary to the receptor.

The image files and the design of the chips are input to an analysis system 120 that, e.g., calls base sequences, or determines expression levels of genes or expressed sequence tags. The expression level of a gene or EST is herein understood to be the concentration within a sample of MRNA or protein that would result from the transcription of the gene or EST. Such analysis techniques are disclosed in WO97/10365, the contents of which are herein incorporated by reference. Base calling techniques are described in WO 95/11995, the contents of which are herein incorporated by reference.

Chip design system 104, analysis system 120 and control portions of exposure system 116, sample preparation system 114, and scanning system 118 may be appropriately programmed computers such as a Sun workstation or IBM-compatible PC. An independent computer for each system may perform the computer-implemented functions of these systems or one computer may combine the computerized functions of two or more systems. One or more computers may maintain chip design database 102 independent of the computers operating the systems of FIG. 1 or chip design database 102 may be fully or partially maintained by these computers.

Figure 2A:
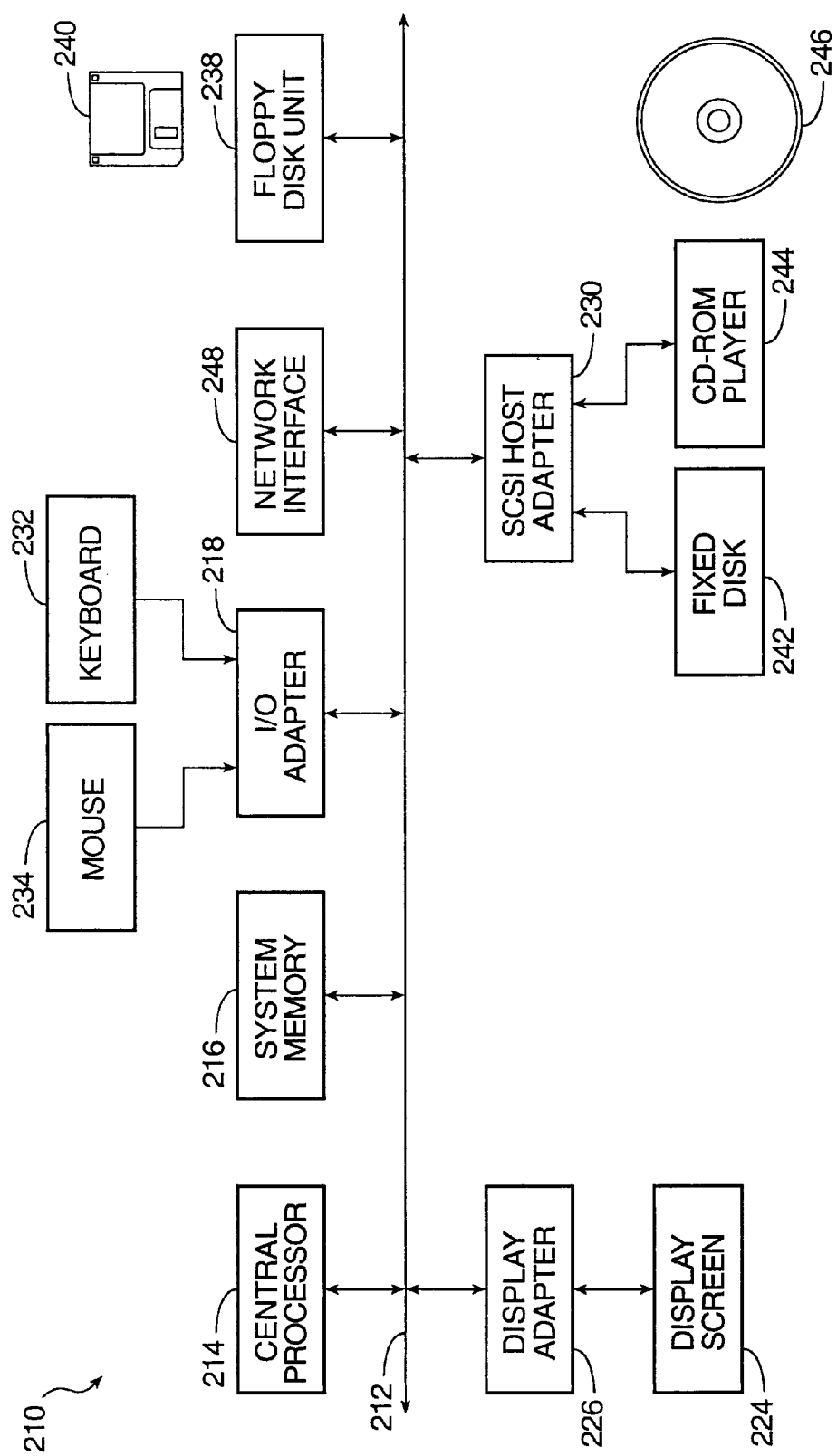
FIG. 2A illustrates a computer system suitable for use in conjunction with the overall system of FIG. 1.

FIG. 2A depicts a block diagram of a host computer system 10 suitable for implementing the present invention. Host computer system 210 includes a bus 212 which interconnects major subsystems such as a central processor 214, a system memory 216 (typically RAM), an input/output (I/O) adapter 218, an external device such as a display screen 224 via a display adapter 226, a keyboard 232 and a mouse 234 via an I/O adapter 218, a SCSI host adapter 236, and a floppy disk drive 238 operative to receive a floppy disk 240. SCSI host adapter 236 may act as a storage interface to a fixed disk drive 242 or a CD-ROM player 244 operative to receive a CD-ROM 246. Fixed disk 244 may be a part of host computer system 210 or may be separate and accessed through other interface systems. A network interface 248 may provide a direct connection to a remote server via a telephone link or to the Internet. Network interface 248 may also connect to a local area network (LAN) or other network interconnecting many computer systems. Many other devices or subsystems (not shown) may be connected in a similar manner.

Also, it is not necessary for all of the devices shown in FIG. 2A to be present to practice the present invention, as discussed below. The devices and subsystems may be interconnected in different ways from that shown in FIG. 2A. The operation of a computer system such as that shown in FIG. 2A is readily known in the art and is not discussed in detail in this application. Code to implement the present invention, may be operably disposed or stored in computer-readable storage media such as system memory 216, fixed disk 242, CD-ROM 246, or floppy disk 240.

Figure 2B:
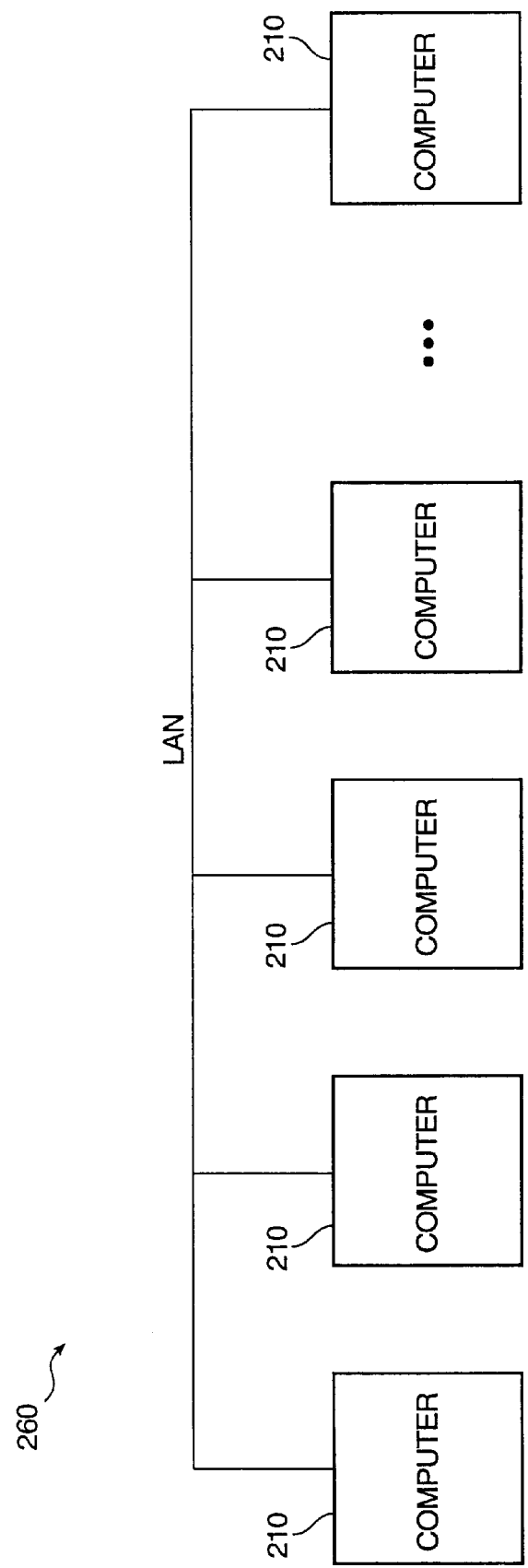
FIG. 2B illustrates a computer network suitable for use in conjunction with the overall system of FIG. 1.

FIG. 2B depicts a network 260 interconnecting multiple computer systems 210. Network 260 may be a local area network (LAN), wide area network (WAN), etc. Bioinformatics database 102 and the computer-related operations of the other elements of FIG. 2B may be divided amongst computer systems 210 in any way with network 260 being used to communicate information among the various computers. Portable storage media such as floppy disks may be used to carry information between computers instead of network 260.

Overall Description of Database

Chip design database 102 is preferably a relational database with a complex internal structure. The structure and contents of chip design database 102 will be described with reference to a logical model that describes the contents of tables of the database as well as interrelationships among the tables. A visual depiction of this model will be an Entity Relationship Diagram (ERD) which includes entities, relationships, and attributes. A detailed discussion of ERDs is found in "ERwin version 3.0 Methods Guide" available from Logic Works, Inc. of Princeton, N.J., the contents of which are herein incorporated by reference. Those of skill in the art will appreciate that automated tools such as Developer 2000 available from Oracle will convert the ERD from FIG. 4 directly into executable code such as SQL code for creating and operating the database.

Figure 3:
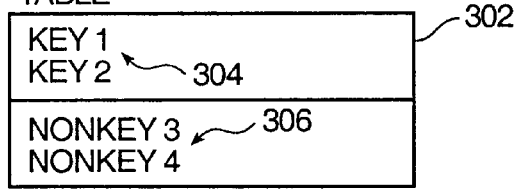
FIG. 3 illustrates a key for interpreting a database model.
Figure 3:
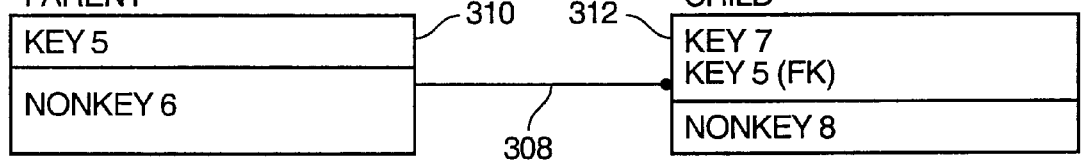
Figure 3:
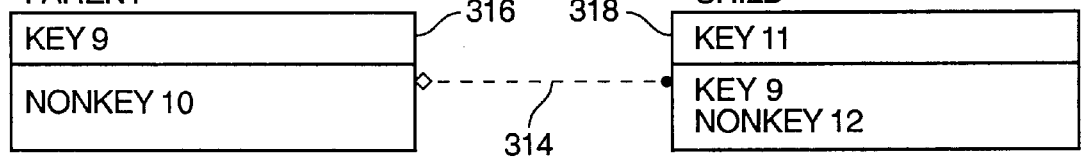

FIG. 3 is a key to the ERD that will be used to describe the contents of chip design database 102. A representative table 302 includes one or more key attributes 304 and one or more non-key attributes 306. Representative table 302 includes one or more records where each record includes fields corresponding to the listed attributes. The contents of the key fields taken together identify an individual record. In the ERD, each table is represented by a rectangle divided by a horizontal line. The fields or attributes above the line are key while the fields or attributes below the line are non-key. An identifying relationship 308 signifies that the key attribute of a parent table 310 is also a key attribute of a child table 312. A non-identifying relationship 314 signifies that the key attribute of a parent table 316 is also a non-key attribute of a child table 318. Where (FK) appears in parenthesis, it indicates that an attribute of one table is a key attribute of another table. For both the non-identifying and the identifying relationship, one record in the parent table corresponds to one or more records in the child table.

At the highest level, chip design database 102 may be understood as providing a relational structure among genomic items, sequence items, and tiling items, as these terms are defined herein by use of example. Genes are characterized by their sequence, location on the genome, and function. Genomic items are herein defined as references to genes, gene clusters, expressed sequence tags (ESTs), and EST clusters by location and/or function but not by sequence. Sequence items are herein defined to be any oligonucleotide sequence or group of oligonucleotide sequences that may or may not by itself have biological meaning. A sequence item may be a long sequence of genomic DNA including more than one exon of biological significance. Alternatively, an exon may include many sequence items. Also, a genomic item may have multiple associated sequence items or groups of sequence items because of changes of sequence information stored in public genomic databases. Genomic items and sequence items are tracked separately by database 102. There is a many-to-many relationship between genomic items and sequence items which is captured by the internal structure of chip design database 102.

Tiling items represent groupings of probes on a chip. A tiling item may be a pair of group of pairs of match and mismatch probes for an expression analysis chip. For sequencing chips, a tiling item may be an atom including a group of probes designed to detect a mutation or call a base at a particular base position. Tiling items are designed to interrogate sequence items, e.g., determine expression or call bases. However, a single tiling item may be used to interrogate more than one sequence item. For example, consider that a sequence item may identify a group of sequences or a single sequence that is longer than the length of a probe. Conversely, certain difficult sequences, e.g., sequences including long runs of the same base, may require more than one tiling item for interrogation. There is thus a many-to-many relationship between sequence item and tiling item and this relation is also captured by the internal design of chip design database 102.

Tiling items include probe pair sets. A probe pair set represents a single sequence on a chip and include probe pairs. Chip design database 102 thus enables one to follow the various interrelationships described above and, e.g., associate a particular probe on a chip with the associated probe pair, probe pair set, tiling item, sequence item, genomic item, etc. The associated genomic item may be a gene cluster associated with a particular gene and an accession number within some biological database. All of these highly complex relationships are preferably captured within chip design database 102.

Chip design database 102 also preferably includes information such as the tiling items contained within any particular chip design. There also may be information about customer orders for a particular chip design including what sequences were to be tested by a particular chip design, who ordered the chip design, etc.

Applications of Chip Design Database

Chip design database 102 is a highly useful tool in designing and tracking existing chip designs. One application is storing intermediate data about genomic items, sequence items, etc. that is input or generated during the course of generating a chip design. Scientists may request that particular genes or sequences be investigated. An intermediate step in determining the chip design will be populating chip design database 102 with the information identifying genes or sequences to be investigated. Since chip design database 102 preserves the information about the genomic items that are investigated by a particular chip design, it is also very useful in finding existing chip designs that are capable of servicing new requests. Also, chip design database 102 may be used after chip design is complete to answer questions about which genomic items and/or sequence items are interrogated by a particular probe or tiling item.

Database Model

Figure 4:
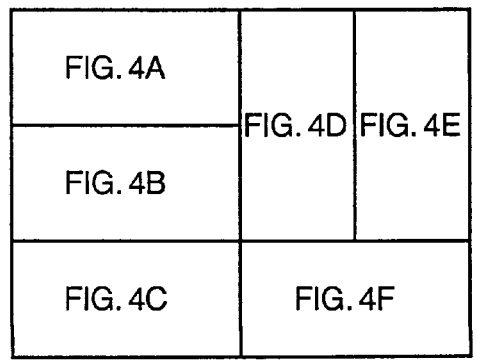
FIG. 4 illustrates a database model for maintaining information for the system and process of FIG. 1 according to one embodiment of the present invention.
Figure 4A:
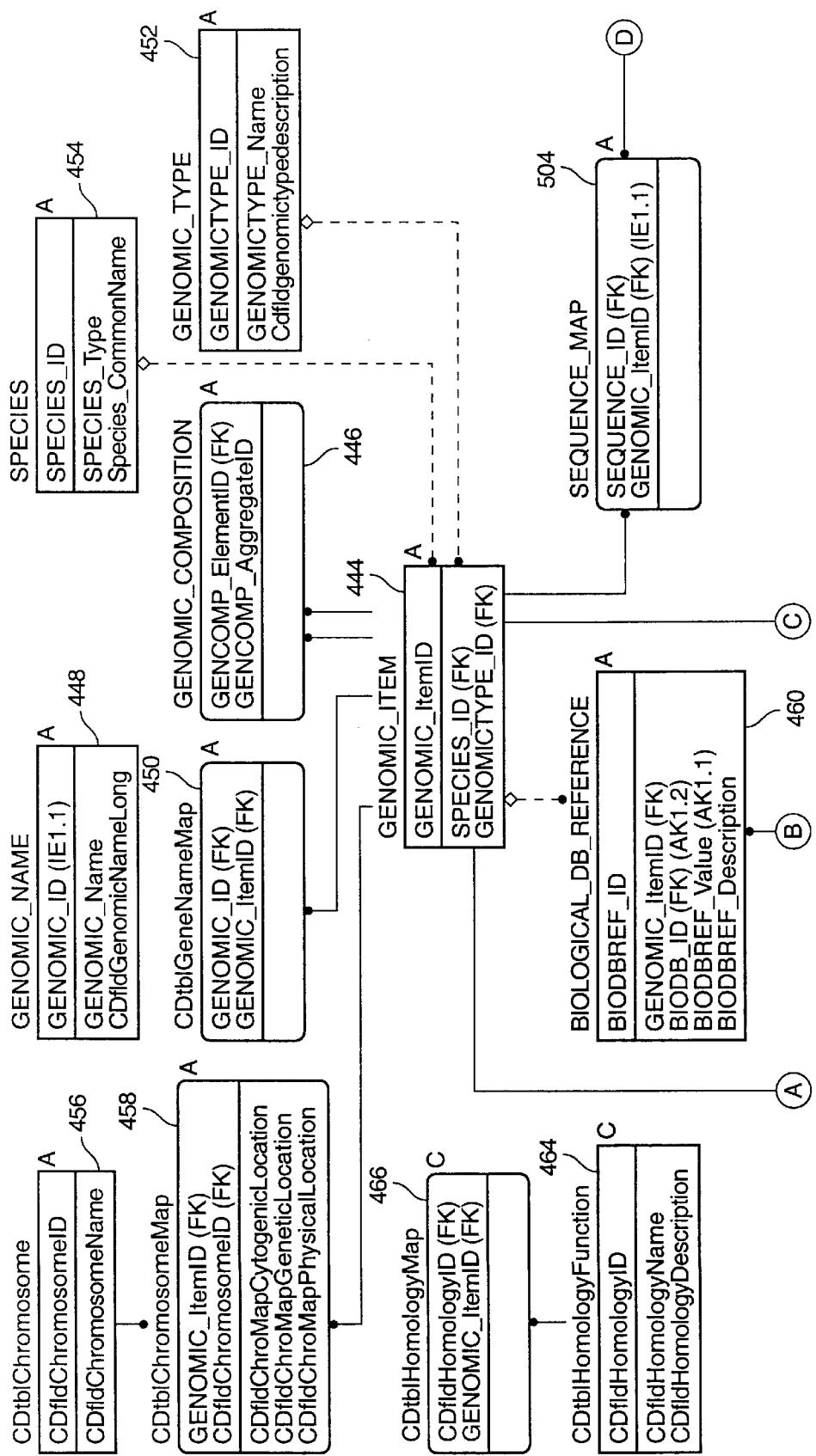
Figure 4B:
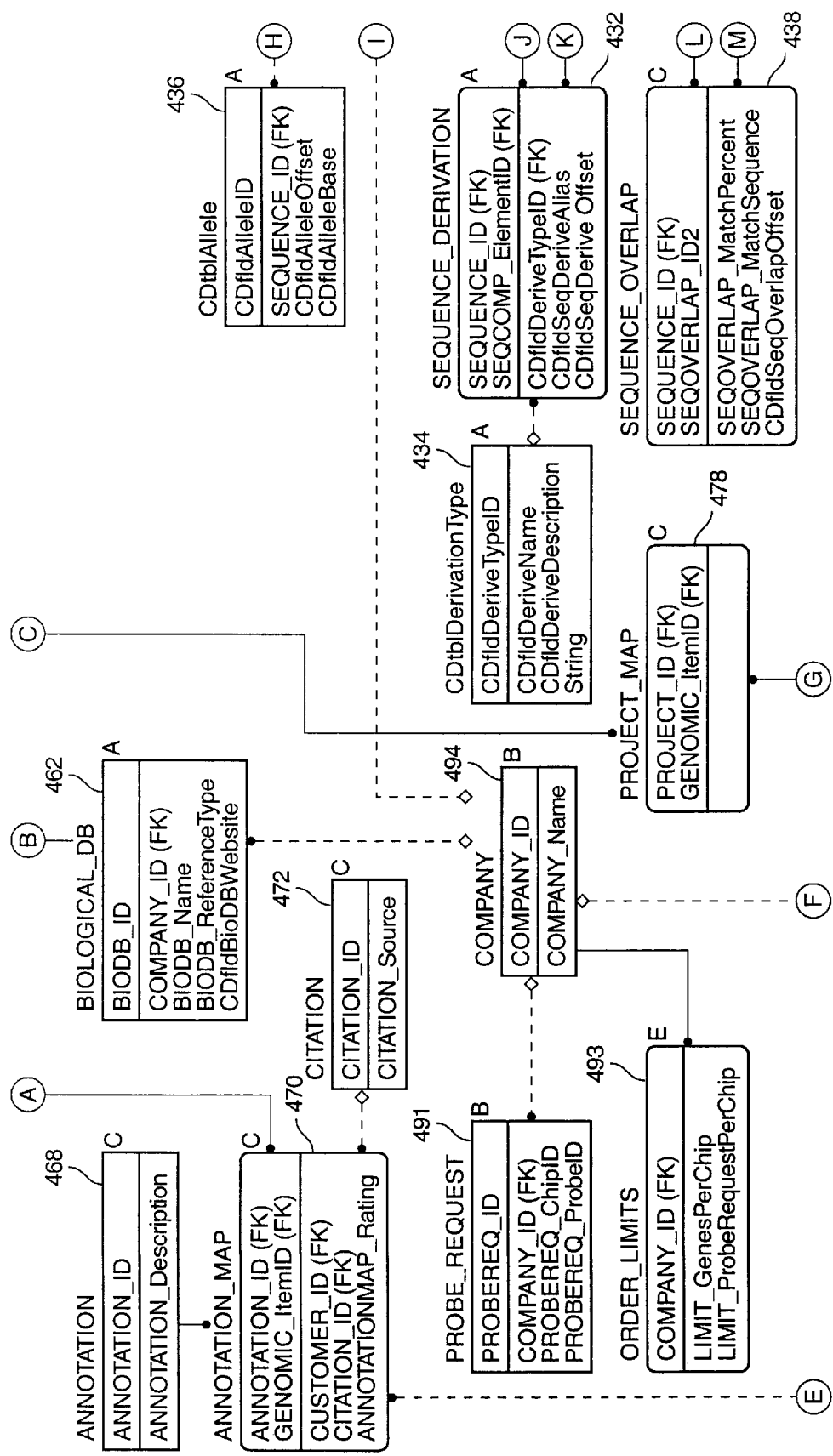
Figure 4C:
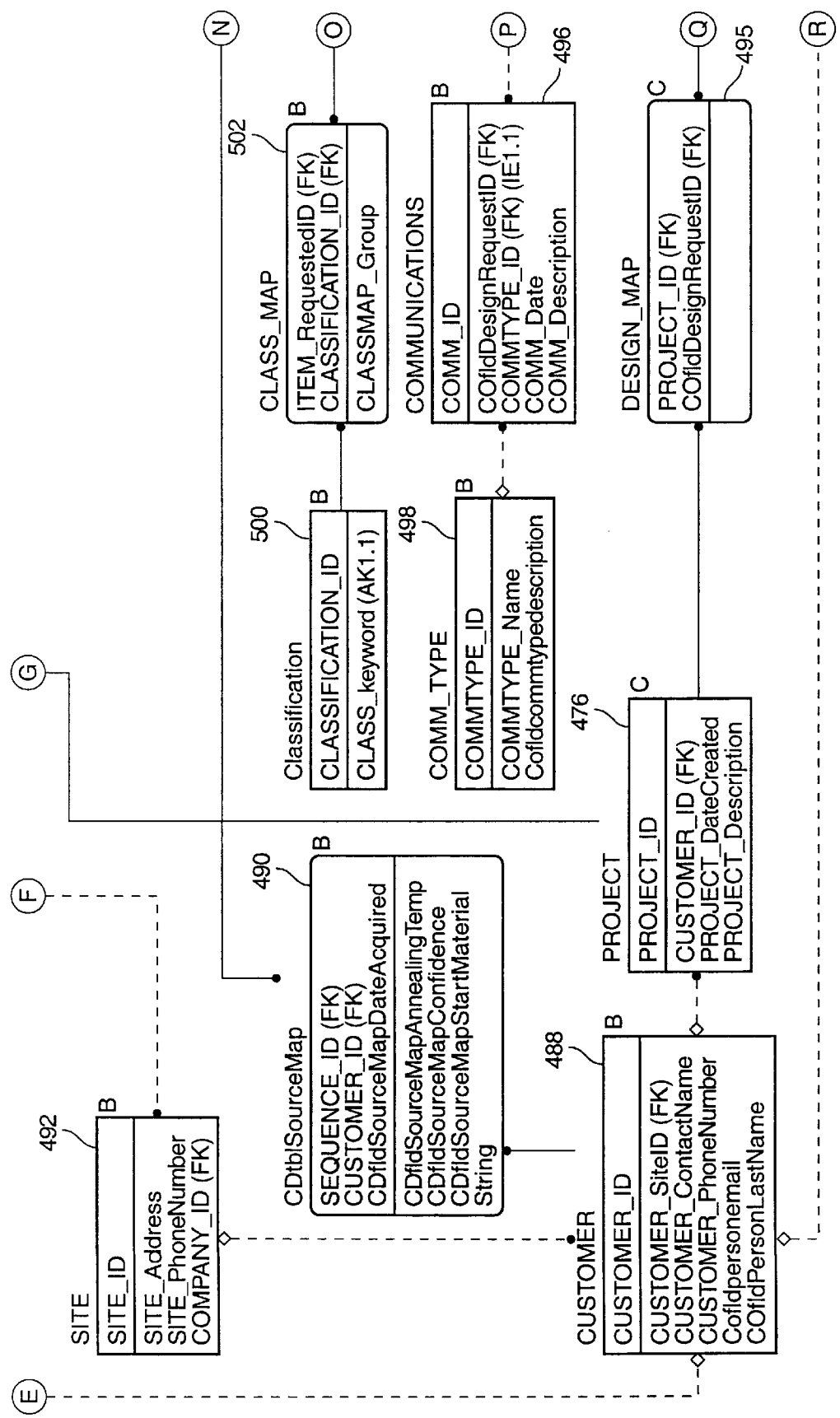
Figure 4D:
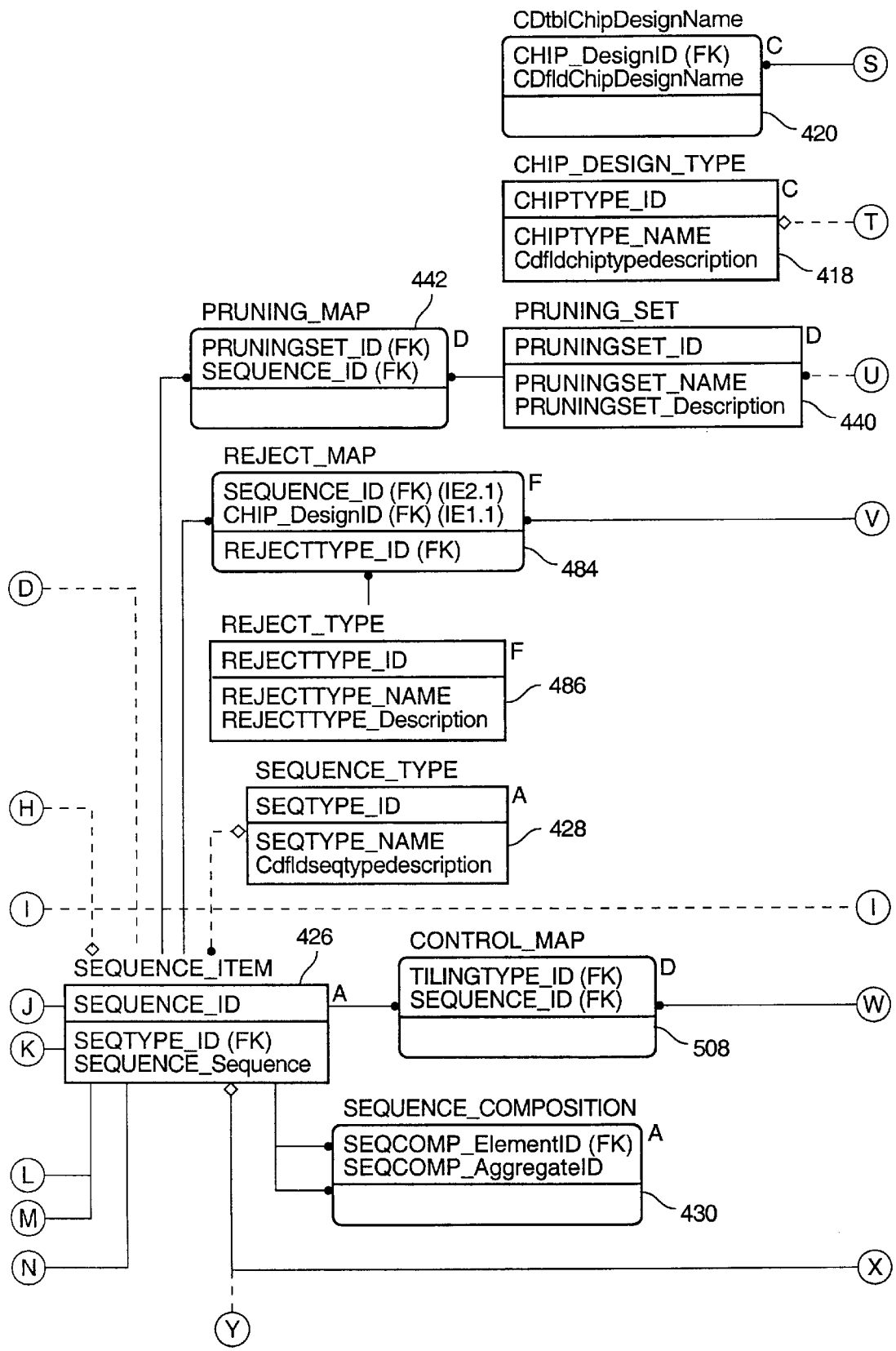
Figure 4E:
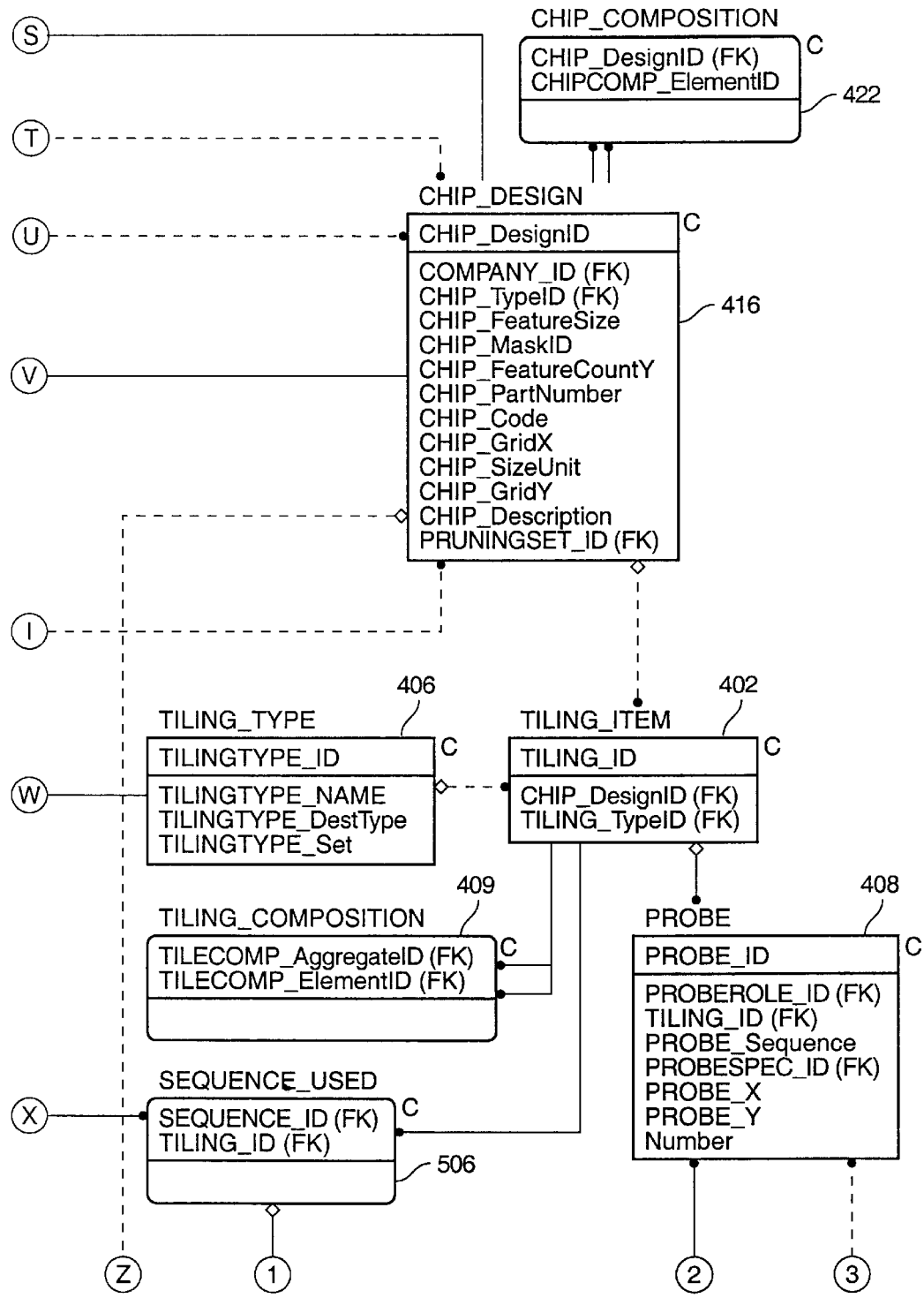
Figure 4F:
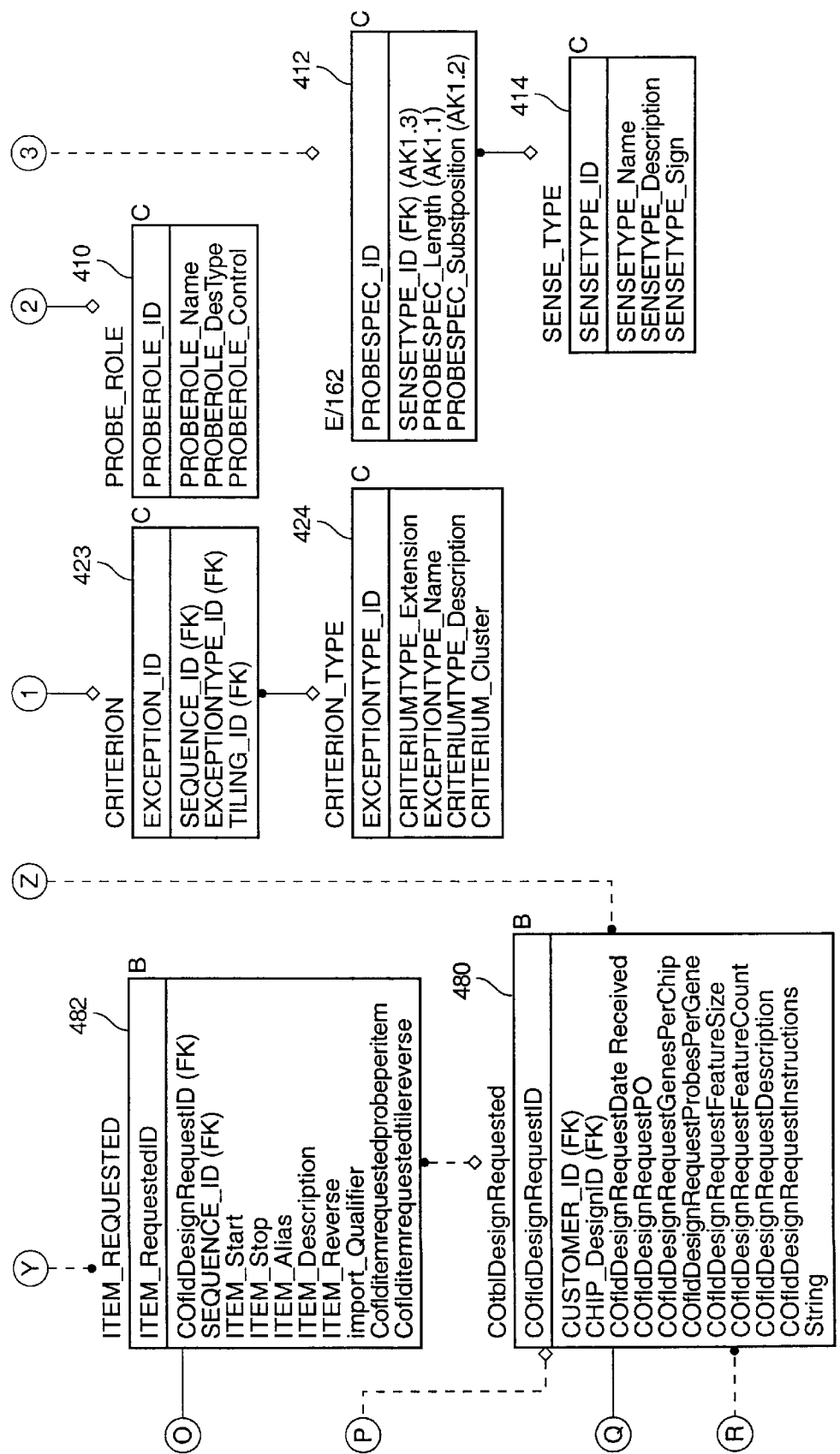

FIG. 4 is an entity relationship diagram (ERD) showing elements of chip design database 102 according to one embodiment of the present invention. Each rectangle in the diagram corresponds to a table in database 102. For each rectangle, the title of the table is listed above the rectangle. Within each rectangle, columns of the table are listed. Above a horizontal line within each rectangle are listed key columns, columns whose contents are used to identify individual records in the table. Below this horizontal line are the names of non-key columns. The lines between the rectangles identify the relationships between records of one table and records of another table. First, the relationships among the various tables will be described. Then, the contents of each table will be discussed in detail.

The tables of database 102 may be understood as belonging to different groups that relate to purpose. In FIG. 4, each table is denoted with a capital letter "A" through "F" to denote membership in a group. Group A includes sequence and biological data. Group B includes design request information. Group C includes chip design information such as which probes are included and how they are laid out. Group D includes design specification information including information used in selecting probes. Group E includes information about compliance to customer contracts for chip design and production. Group F includes information about sequences requested but not included in a final chip design because of difficulty in selecting probes that would be effective in investigating them.

The interrelationships and general contents of the tables of database 102 will be described first. Then a chart will be presented listing and describing all of the fields of the various tables.

A tiling item table 402 lists the various tiling items. Each record in tiling item table 402 identifies a tiling item for a particular chip design. Each tiling item has an associated tiling item type listed in a tiling item type table 406. Examples of tiling item type include "probe pairs" which would identify a perfect match—mismatch probe pair or "atom" which would indicate a group of probes used for determining a mutation or calling a base at a particular base position. Each tiling item has one or more associated probes which are listed in a probe table 408.

A tiling item may itself be an aggregation of other tiling items. A tiling composition table 409 includes records that associate aggregate tiling items with the tiling items they include.

Associated with each probe listed in probe table 408 is a probe role record in a probe role table 410. The probe role record tells, e.g., if a particular probe in a perfect match mismatch pair is itself the perfect match or the mismatch. Further associated with each probe is a probe specification record in a probe specification table 412. The probe specification record tells the length of the probe and the orientation of the probe. The orientation of the probe (sense or antisense) is identified within the probe specification record by reference to a record in a sense type table 414 which lists both orientations.

A chip design table 416 lists chip designs. Associated with each chip design is a plurality of tiling items in tiling item table 402. Also associated with each chip design is a chip design type as listed in a chip design type table 418. Examples of chip design types are "expression analysis" or "mutation detection." Each chip design may have many associated chip design names listed in a chip design name table 420. These names may include informal names used within the organization or formal names used in formal interorganization communications.

Chip designs may be aggregated into chip design sets which are listed in a chip composition table 422. Each record of chip composition table 422 identifies a chip design set which may include more than one chip design listed in chip design table 416. A chip design set may characterize a group of chips used together for a particular purpose such as identifying expression of oncogenes or tumor suppressors in humans.

An exception table 424 lists sequences whose investigation was requested but for which optimal probes were not included in the design. Each exception is associated with a particular combination of sequence and tiling item and has an associated exception type listed in an exception type table 426. One type of exception, referred to as an "R" exception is noted when preferred rules for probe selection have not been followed because they would not result in an adequate set of probes in the chip design for a particular sequence. An "S" exception denotes that the sequence is very similar to another sequence and that sequences had to be grouped together to find acceptable probe sets so that certain probes interrogate more than one sequence. An "I" exception indicates that the probe set is incomplete, although the probes that are included in the set interrogating the sequence are of high quality. A "B" exception indicates that all probe selection rules have been dropped and that the probes are of low quality. A "G" indicates that the sequence overlaps with another sequence.

There is a sequence item table 426 that lists all the sequence items of chip design database 102. Associated with each listed sequence item is a sequence type from sequence type table 428. Examples of sequence type include "sequence" and "group of sequences." A sequence composition table 430 is used to aggregate sequences into groups of sequences. Each group listed in sequence composition table 430 has associated sequences in sequence item table 426.

There is a sequence derivation table 432 which lists derivations used to transform one sequence listed in sequence item table 426 into another. Each derivation has a derivation type listed in a derivation type table 434. Examples of derivation types include "removal of ambiguities," or "change in GenBank information." An allele table 436 lists polymorphisms for some of the sequences listed in sequence item table 432.

A sequence overlap table 438 lists overlaps between sequences of sequence item table 426. These overlaps are important to know for the probe selection process. The overlaps are determined by a process known as blast comparison. The result of a blast comparison is a description of the match quality between the compared sequences. This match quality is stored in sequence overlap table 438.

During the chip design process, sequences may be the basis for creating tiling items. Sequence information is also the basis for pruning the set of probes that are included in a chip design. Pruning is a step of probe selection. Objectives of pruning may include: assuring that no probe is a duplicate of another probe in a probe pair set, assuring that no probe is the same as any other probe in a chip or set of chips, or assuring that a probe is not a duplicate of any probe that would be used to interrogate a set of sequences larger than the set investigated by a chip or set of chips. For example, it may be useful once the entire human genome is known to prune probe sets so that no probe is used that would interrogate more than one sequence in the genome. The more that is pruned against, the higher the quality of the resulting chip design is since ambiguity in analysis results is greatly reduced. To facilitate pruning, chip database 102 provides a pruning set table 440 which lists pruning sets. Each pruning set has an associated chip design in chip design table 416. A pruning map table 442 lists correlations between particular sequence items and pruning sets and implements the many-to-many relation that exists between sequence item table 426 and pruning set table 440.

A genomic item table 444 lists genomic items. Each listed genomic item may be a gene or EST or an aggregate of genes or ESTs. A genomic composition table 446 lists the relationships between aggregations of genes and/or ESTs and their components. A genomic name table 448 lists names of genomes. Each name may apply to more than one genome. Similarly, each genome may have more than one name. A genomic name map table 450 implements the many-to-many relationships between genomes and names.

A genomic type table 452 lists the various types of genome such as "gene," "gene cluster," "EST," and "EST cluster." Each genomic item in genomic item table 444 has an associated genomic type in genomic type table 452. A species table 454 lists the species associated with the genomic items. Each genomic item in genomic item table 444 has an associated species in species table 454.

It is often useful to know the position of a genomic item in a chromosome. A chromosome table 456 lists various chromosomes. Each record in a chromosome map table 458 indicates which chromosome a genomic item is located in and where on the chromosome the genomic item would be found.

It is also useful to store information about database references for genomic items. The records of biological database reference table 460 each include information as would be found in one database about one genomic item. The databases themselves are listed in a biological database table 462. Representative databases include GenBank, Entrez, and TIGR.

Genomic items are themselves related to one another by functional homology. Genomic items may be grouped by the functions performed by proteins that result from their expression. A homology function table 464 lists different functions in a cell. A homology map table 466 lists associations between the listed homologies and genomic items listed in genomic item table 444.

Genomic items listed in genomic item table 444 may also have associated annotation information. An annotation table 468 lists annotations for genomic items. Each record in an annotation map table 470 associates an annotation and a genomic item. A comment found in an annotation may be backed up by a citation to the literature listed in a citation table 472.

Genomic items may be grouped into sets corresponding to projects where each project has a particular investigative objective. For example one project may investigate genes relating to high blood pressure while another project investigates genes relating to breast cancer. Typically, a project will be the impetus for designing a chip or a set of chips. A project table 476 lists such projects. A project map table 478 lists associations between projects and genomic items and like the other map tables implements a many-to-many relationship between genomic items and projects.

The chip design process may originate with a project assignment which specifies genomic items, or may alternatively originate with a design request that specifies sequences to be interrogated by probes on the chip. A design request table 480 lists such design requests. Each design request may have many associated design request items listed in a design request item table 482. The records of design request item table 482 each identify a requested sequence item.

All requested sequences may or may not fit in the final chip design. If a requested sequence is not found in a chip design, this is recorded in a reject map table 484. Each record in reject map table 484 identifies a sequence that was requested to be included in a particular chip design but left out. Each such reject record has an associated reject type selected from the types listed in a reject type table 486.

Associated with each design request or project is a customer as listed in a customer table 488. Each customer may have one or more associated design requests, annotations, or projects as listed in tables 480, 468, and 476 respectively. A customer may also be the source of one or more sequence items as found in a sequence item table 426. A source map table 490 implements the many-to-many relationship between sequence items and customers. Each customer is associated with a site as recorded in a site table 492.

There may also be associations between design requests and projects. Projects may have one or more associated design requests and design requests may have one or more associated projects. A design map table 493 lists associations between design requests and projects.

Companies may have one or more sites and are listed in a company table 494. Biological databases listed in biological database table 462 may be proprietary to companies listed in company table 494. By providing a relationship between these two tables, chip design database 102 allows the chip designer to keep track of genomic item information that should be kept proprietary to particular orderers. Source map table 490 similarly assists in maintaining the necessary confidentiality for customer-originated sequence information. A company may request specific probes to be included in a chip. These requests are listed in a probe request table 491. An order limits table 493 lists the contractual limitations that apply to chip design work to be done for particular companies. For example, a company may be limited to investigate a certain number of genes per chip, or be limited to request a certain number of probes per chip.

A communications table 496 lists communications between the chip designer and customer about a particular design request. Each design request may have one or more associated communications. Each communication listed in communications table 496 has an associated communications type as listed in a communications type table 498. Different communication types may correspond to different stages in the process. For example, the different types may include "chip request," "sequences updated," "sequences incomplete," etc.

A classification table 500 lists classifications of item requests. Such classifications represent functional hierarchies. Classifications may include, e.g., tissue types or protein family names. A classification map table 502 associates item requests with classifications.

The many-to-many relationship between genomic items and sequence items is implemented by a sequence map table 504 which lists associations between genomic items and sequence items. The many-to-many relationship between sequence items and tiling items and thus probes is implemented by a sequence used map 506 which lists associations between sequence items and tiling items. A control map table 508 similarly implements a many-to-many relationship between sequence items and tiling types.

Database Contents

The contents of the tables introduced above will now be presented in greater detail in the following chart.

| TABLE | FIELD | CONTENTS |
|---|---|---|
| CDtblChromosome | CDfldChromosomeID | Identification number for chromosome. |
| | CDfldChromosomeName | Name of chromosome. |
| CDtblChromosomeMap | GENOMIC_ItemD(FK) | Reference to genomic item in genomic item table. |
| | CDfldChromosomeD(FK) | Reference to chromosome table. |
| | CDfldChroMapCytogenicLocation | Cytogenic location. |
| | CDfldChroMapGeneticLocation | Genetic location. |
| | CDfldChroMapPhysicalLocation | Physical location of genomic item on chromosome. |
| GENOMIC NAME | GENOMIC ID(IE1.1) | Reference to genomic item table. |
| | GENOMIC Name | Name of genome. |
| | CDfldGenomicNameLong | Longer version of genomic name. |
| SPECIES | SPECIES ID | Species identification. |
| | SPECIES Type | Type of species. |
| | SPECIES CommonName | Common name of species. |
| CDtblGeneNameMap | GENOMIC ID(FK) | Reference to genomic name table. |
| | GENOMIC ItemID(FK) | Reference to genomic item table. |
| CDtblHomologyMap | GENCOMP_Element(FK) | Points to genomic item in genomic item table. |
| | GENCOMP AggregateID | Identifies aggregation of genomic items. |
| GENOMIC TYPE | GENOMICTYPE ID | Identifier for genomic type. |
| | GENOMICTYPE Name | Name of genomic type. |
| | CDfldgenomictypedescription | Description of genomic type. |
| GENOMIC ITEM | GENOMIC ItemID | Genomic item identifier. |
| | SPECIES ID(FK) | Reference to species table. |
| | GENOMIC ItemId(FK)(IE1.1) | Reference to genomic type table. |
| CDtblHomologyMap | CDfldHomologyID(FK) | Homology identifier. |
| | GENOMIC itemId(FK) | Reference to genomic item table. |
| CDtblHomologyFunction | CDfldHomologyID | Homology identifier. |
| | CDfldHomologyName | Name of homology. |
| | CDfldHomologyDescription | Description of homology. |
| BIOLOGICAL_DB_REFERENCE | BIODBEF_ID | Identifier for biological database reference. |
| | GENOMIC itemID(FK) | Reference to genomic item table. |
| | BIODB ID(FK)(AK1.2) | Reference to biological dababase table. |
| | BIODBREF_Value(AK1.1) | Reference value, e.g., accession number. |
| | BIODBREF Description | Description of database reference. |
| BIOLOGICAL DB | BIODBREF ID | Biological database identifier. |
| | COMPANY ID(FK) | Reference to company table. |
| | BIODB Name | Name of database. |
| | BIODB ReferenceType | Type of reference. |
| | CDfldBioDBWebSite | Website for database. |
| ANNOTATION | ANNOTATION ID | Annotation identifier. |
| | ANNOTATION Description | Description of annotation. |
| ANNOTATION MAP | ANNOTATION ID(FK) | Reference to annotation table. |
| | GENOMIC ItemID(FK) | Reference to genomic item table. |
| | CUSTOMER ID(FK) | Reference to customer table |
| | CITATION ID(FK) | Referenct to citation table |
| | ANNOTATIONMAP Ratng | Indication of quality of annotation. |
| CITATION | CITATION ID | Citation identifier. |
| | CITATION Source | Source of citation. |
| SEQUENCE ITEM | SEQUENCE ITEM | Sequence identifier. |
| | SEQTYPE ID(FK) | Reference to sequence type table. |
| | SEQUENCE Sequence | Sequence (may be very long field). |
| SEQUENCE MAP | SEQUENCE ID(FK) | Reference to sequence item table. |
| | GENOMIC ItemID(FK)(IE1.1) | Reference to genomic item table. |
| CDtblAllele | CDfldAlleleID | Allele identifier. |
| | SEQUENCE ID(FK) | Reference to sequence item table. |
| | CDfldAlleleOffset | Position of polymorphism |
| | CDfldAlleleBase | Base defined by polymorphism. |

-continued

| TABLE | FIELD | CONTENTS |
|---|---|---|
| E/198 | SEQUENCE ID(FK)(IE2.1) | Reference to sequence item table. |
| | CHIP DesignID(FK)(E1.1) | Reference to chip design table. |
| | REJECTTYPE ID(FK) | Reference to reject type table. |
| E/200 | REJECTTYPE ID | Reject type identifier. |
| | REJECTTYPE Name | Name of reject type. |
| | REJECTTYPE Description | Description of reject type. |
| SEQUENCE TYPE | SEQTYPE ID | Sequence type identifier. |
| | SEQTYPE Name | Name of sequence type. |
| | CDfldseqtypedescription | Description of sequence type. |
| SEQUENCE DERIVATION | SEQUENCE ID(FK) | Original sequence. |
| | SEQCOMP ElementID(FK) | Derived Sequence. |
| | CDfldDeriveTypeID(FK) | Reference to derivation type table |
| | CDfldSeqDeriveAlias | Suffix attached to name of derived sequence. |
| | CDfldSeqDeriveOffset | Offset between original sequence and derived sequence. |
| CDtblDerivation Type | CDfldDeriveTypeID | Derivation type identifier. |
| | CDfldDeriveName | Name of derivation type. |
| | CDfldDeriveDescription | Description of derivation type. |
| | String | Suffix associated with derivation type. |
| SEQUENCE OVERLAP | SEQUENCE ID (FK) | First sequence compared. |
| | SEQSEQOVERLAP ID2 | Second sequence compared. |
| | SEQOVERLAP_MatchPercent | Percentage match between compared sequences. |
| | SEQOVERLAP_MatchSequence | Sequencing common between two compared sequences. |
| | CDfldSeqOverlapOffset | Offset value if second compared sequences an offset from first compared sequence. |
| SEQUENCE COMPOSITION | SEQCOMP_ElementID(FK) | Identifier of sequence included in aggregate. |
| | SEQCOMP AggregateID | Identifier of aggregate of sequences. |
| PRUNING MAP | PRUNINGSET ID(FK) | Pruning set identifier. |
| | SEQUENCE ID(FK) | Reference to sequence item table. |
| PRUNING SET | PRUNINGSET ID | Pruning set identifier. |
| | PRUNINGSET NAME | Name of pruning set. |
| | PRUNINGSET Description | Description of pruning set. |
| CHIP DESIGN | CHIP DesignID | Chip design identifier. |
| | COMPANY ID(FK) | Reference to company table. |
| | CHIP TypeID(FK) | Reference to chip type table. |
| | CHIP_FeatureSize | X dimension size of chip features, e.g., 25 or 50 μm. |
| | CHIP_MaskID | Mask identifier associated with mask for chip |
| | CHIP FeatureCountY | Feature size and Y direction. |
| | CHIP PartNumber | Part number to identify chip. |
| | CHIP Code | Another chip designator. |
| | CHIP GridX | Number of cells in the X direction. |
| | CHIP_SizeUnit | Units used for feature size, typically microns. |
| | CHIP GridY | Number of cells in the Y direction. |
| | Chip Description | Description of chip. |
| | PRUNINGSET ID(FK) | Reference to pruning set table. |
| CHIP DESIGN TYPE | CHIPTYPE ID | Chiptype identifer. |
| | CHIPTYPE Name | Name of chip type. |
| | CDfldchiptypedescription | Description of chip type. |
| CDtblChipDesignName | CHIP DesignID(FK) | Reference to chip design table. |
| | CDfldChipDesignName | Name of chip design. |
| CHIP_COMPOSITION | CHIP DesignID(FK) | Identifier of chip set. |
| | CHIPCOMP ElementID | Identifier of chip in chip set. |
| TILING ITEM | TILING ID | Tiling item identifier. |
| | CHIP DesignID(FK) | Reference to chip design table. |
| | TILING TypeID(FK) | Reference to tiling type table. |
| TILING TYPE | TILINGTYPE ID | Tiling type identifier. |
| | TILINGTYPE Name | Name of tiling type. |
| | TILINGTYPE DesType | Code for tiling type. |
| | TILINGTYPE Set | Description of tiling type. |
| CONTROL MAP | TILING TYPE ID(FK) | Reference to tiling type table. |
| | SEQUENCE ID(FK) | Reference to sequence item table. |
| TILING_COMPOSITION | TILECOMP_AggregateID(FK) | Identifier for aggregation of tiling items. |
| | TILECOMP_ELEMENTID(FK) | Identifier for tiling item within aggregation. |
| PROBE | PROBEID | Probe identifier. |
| | PROBEROLE ID(FK) | Reference to probe role table. |
| | TILING ID | Reference to tiling item table. |
| | PROBE Sequence | Probe sequence. |

-continued

| TABLE | FIELD | CONTENTS |
|---|---|---|
| | PROBESPEC ID(FK) | Probe specification identifier. |
| | PROBE X | X position of probe on chip. |
| | PROBE Y | Y position of probe on chip. |
| | Number | Sequence position of probe |
| PROBE ROLE | PROBEROLE ID | Probe role identifier. |
| | PROBEROL_Name | Name of probe roll, e.g., perfect match or mismatch. |
| | PROBEROLE DesType | Code representing probe roll name. |
| | PROBEROL_Control | Indicates whether probe is a control probe. |
| PROBE SPEC | PROBESPEC ID | Probe specification identifier. |
| | SENSETYPE_ID(FK)(AK1.3) | Sense type indication, e.g., sense or antisense; reference to sense type table. |
| | PROBESPEC Length(AK1.1) | Length of probe. |
| | PROBESPEC_SubatPosition (AK1.2) | Position at which mismatch is made for a mismatch probe. |
| SENSE TYPE | SENSETYPE ID | Sense type identifier. |
| | SENSETYPE_Name | Name of sense type, e.g., sense or antisense. |
| | SENSETYPE Description | Longer version of sense or antisense. |
| | SENSETYPE_Sign | Positive or negative, depending on whether sense or antisense. |
| SEQUENCE USED | SEQUENCE ID(FK) | Reference to sequence item table. |
| | TILING ID(FK) | Reference to tiling item table. |
| CRITERIAN | EXCEPTION ID | Exception identifier. |
| | SEQUENCE ID(FK) | Reference to sequence item table. |
| | EXCEPTIONTYPE ID(FK) | Reference to exception type table. |
| | TILING ID(FK) | Reference to tiling item table. |
| CRITERIAN2 | EXCEPTIONTYPE ID | Exception type identifier. |
| | CRITERIUMTYPE Extension | Suffix to identify criterium type. |
| | EXCEPTIONTYPE Name | Name of criterium type. |
| | CRITERIUMTYPE Description | Description of criterium type. |
| | CRITERIUM_Cluster | whether criterium type is part of a cluster. |
| CUSTOMER | CUSTOMER ID | Customer identifier. |
| | CUSTOMER SiteID(FK) | Reference to site table. |
| | CUSTOMER ContactName | Name of customer contact. |
| | CUSTOMER PhoneNumber | Phone number of customer contact. |
| | Cofdpersonemail | E-mail address of customer contact. |
| | COfldPersonLastName | Last name of customer contact. |
| SITE | SITE ID | Site identifier next row. |
| | SITE Address | Address of site. |
| | SITE PhoneNumber | Phone number of site. |
| | COMPANY ID(FK) | Reference to company table. |
| COMPANY | COMPANY ID | Company identifier. |
| | COMPANY Name | Name of company. |
| PROBE REQUEST | PROBEREQ ID | Probe request identifier. |
| | COMPANY ID(FK) | Reference to company table. |
| | PROBEREQ_ChipID | Chip that probe request is made for, reference to chip design table. |
| | PROBEREQ_ProbeId | Identifier of probe that was requested, reference to probe table. |
| OUTER LIMITS | COMPANY ID(FK) | Reference to company table. |
| | LIMIT GenesPerChip | Maximum number of genes per chip. |
| | LIMIT ProbeRequestPerChip | Maximum number of probes per chip. |
| CDtblSourceMap | SEQUENCE ID(FK) | Reference to sequence item table. |
| | CUSTOMER ID(FK) | Reference to customer table. |
| | CDfldSourceMapDateAcquired | Date source map acquired. |
| | CDfldSourceMapAnnealing Temp | Annealing temperature for sequence. |
| | CDfldSourceMapConfidence | Confidence level in sequence map. |
| | CDfldSourceMapStartMaterial | Pertains to method of creation of map. |
| | String | Comment. |
| PROJECT | PROJECT ID | Project identifier. |
| | CUSTOMER ID(FK) | Reference to customer table. |
| | PROJECT DateCreated | Date of project creation. |
| | PROJECT Description | Description of project. |
| PROJECT MAP | PROJECT ID(FK) | Reference to project table. |
| | GENOMIC ItemId(FK) | Reference to genomic item table. |
| COtblDesignRequest | COfldDesignRequestID | Design request identifier. |
| | CUSTOMER ID(FK) | Customer identifier. |
| | CHIP DesignID(FK) | Reference to chip design table. |
| | COMMTYPE_IDCOfldDesignRequestDateReceived | Date request received. |
| | COMMTYPE_NameCOfldDesignRequestPO | Purchase order number. |
| | CofldcomCOfldDesignRequestGenesPerChip | Number of genes per chip requested. |

-continued

| TABLE | FIELD | CONTENTS |
|---|---|---|
| | COfldDesignRequest ProbesPerGene | Number of probes per gene requested. |
| | COfldDesignRequestFeatureSize | Feature size requested, e.g., 25 or 50 $\mu$m |
| | COfldDesignRequestFeatureCount | How many features will fit on chip. |
| | COfldDesignRequestDescription | Description of requested chip. |
| | COfldDesignRequestInstructions String | Customer instructions. Orientation of target sequences that are to be read with the chip. |
| DESIGN MAP | PROJECT ID(FK) | Reference to project table. |
| | COfldDesignRequestID(FK) | Reference to design request table. |
| COMMUNICATIONS | COMM ID | Communications identifier. |
| | COfldDesignRequestID(FK) | Reference to design request table. |
| | COMMTYPE ID(FK)(IE1.1) | Reference to communication type table. |
| | COMM Date | Date of communication. |
| | COMM Description | Description of communication. |
| COMM TYPE | COMMTYPE ID | Communication type identifier. |
| | COMMTYPE Name | Name of communication type. |
| | Cofldcommtypedescription | Description of communication type. |
| ITEM REQUESTED | ITEM RequestedId | Requested item identifier. |
| | COfldDesignRequestID(FK) | Reference to design request table. |
| | SEQUENCE ID(FK) | Reference to sequence item table. |
| | ITEM_Start | Permissible starting point in submitted sequence. |
| | ITEM Stop | Permitted stopping point in sequence. |
| | ITEM Alias | Another name for specified sequence. |
| | ITEM Description | Description of sequence. |
| | ITEM_Reverse | Whether sequence is to be reversed before placement on chip. |
| | import Qualifier | Import qualifier?? |
| | CofldItemrequestedprobeperitem | Override to number of probes per gene in design request table. |
| | Coflditemrequestedtilereverse | Whether particular sequence is to be tiled in sense or antisense direction. |
| Classification | CLASSIFICATION ID | Classification identifier. |
| | CLASS Keyword(AK1.1) | Description of classification. |
| CLASS MAP | ITEM RequestedID(FK) | Reference to item request table. |
| | CLASSIFICATION ID(FK) | Reference to classification table. |
| | CLASSMAP_Group | Grouping together of classification specified by customer. |

It is understood that the examples and embodiments described herein are for illustrative purposes only and that various modifications or changes in light thereof will be suggested to persons skilled in the art and are to be included within the spirit and purview of this application and scope of the appended claims. For example, tables may be deleted, contents of multiple tables may be consolidated, or contents of one or more tables may be distributed among more tables than described herein to improve query speeds and/or to aid system maintenance. Also, the database architecture and data models described herein are not limited to biological applications but may be used in any application. All publications, patents, and patent applications cited herein are hereby incorporated by reference.

What is claimed is:

1. A computer-readable storage medium having stored thereon:
   a relational database comprising:
      a probe table including a plurality of probe records, each of said probe records specifying a polymer probe for use in one or more polymer probe arrays;
      a sequence item table including a plurality of sequence item records, each of said sequence item records specifying a nucleotide sequence to be investigated in said one or more polymer probe arrays; and
      wherein there is a many-to-many relationship between said probe records and said sequence item records and at least one sequence item record corresponds to more than one probe record and at least one probe record corresponds to more than one sequence item record.

2. The medium of claim 1 wherein said relational database further comprises:
   a tiling item table including a plurality of tiling item records, each of said tiling item records having an aggregation relationship with said probe records so that each tiling item record has many associated probe records.

3. The medium of claim 1 wherein said relational database further comprises:
   a genomic item table including a plurality of genomic item records, each of said genomic item records specifying a genomic item to be investigated by said one or more polymer probe arrays; and
   wherein there is a many to many relationship between genomic item records and sequence item records.

4. The medium of claim 1 wherein said relational database further comprises:
   a chip design table including a plurality of chip design records, each of said chip design records specifying a design of a chip including a subset of said plurality of probe records.

5. A computer implemented method for operating a relational database comprising:
   creating a probe table including a plurality of probe records, each of said probe records specifying a polymer probe for use in one or more polymer probe arrays;
   creating a sequence item table including a plurality of sequence item records, each of said sequence item records specifying a nucleotide sequence to be investigated in said one or more polymer probe arrays;

storing data in said probe table and said sequence item table; and wherein there is a many-to-many relationship between said probe records and said sequence item records and at least one sequence item record corresponds to more than one probe record and at least one probe record corresponds to more than one sequence item record.

6. The method of claim 5 further comprising the step of:

creating a tiling item table including a plurality of tiling item records, each of said tiling item records having an aggregation relationship with said probe records so that each tiling item record has many associated probe records.

7. The method of claim 5 further comprising the step of:

creating a genomic item table including a plurality of genomic item records, each of said genomic item records specifying a genomic item to be investigated by said one or more polymer probe arrays; and wherein there is a many to many relationship between genomic item records and sequence item records.

8. The method of claim 5 further comprising the step of:

creating a chip design table including a plurality of chip design records, each of said chip design records specifying a design of a chip including a subset of said plurality of probe records.

9. A computer system comprising:

a processor; and a storage medium storing a relational database accessible by said processor, said storage medium having stored thereon:

a relational database comprising:

a probe table including a plurality of probe records, each of said probe records specifying a polymer probe for use in one or more polymer probe arrays;

a sequence item table including a plurality of sequence item records, each of said sequence item records specifying a nucleotide sequence to be investigated in said one or more polymer probe arrays; and wherein there is a many-to-many relationship between said probe records and at least one sequence item record corresponds to more than one probe record and at least one probe record corresponds to more than one sequence item record.

* * * * *